United States Patent [19]
Ahmed et al.

[11] Patent Number: 5,871,595
[45] Date of Patent: Feb. 16, 1999

[54] LOW MODULUS BIOCOMPATIBLE TITANIUM BASE ALLOYS FOR MEDICAL DEVICES

[75] Inventors: Toseef Ahmed, Clemson; Henry J. Rack, Pendleton, both of S.C.

[73] Assignee: Osteonics Corp., Allendale, N.J.

[21] Appl. No.: 792,091

[22] Filed: Jan. 31, 1997

Related U.S. Application Data

[63] Continuation of Ser. No. 323,453, Oct. 14, 1994, abandoned.
[51] Int. Cl.⁶ .................................................. C22C 14/00
[52] U.S. Cl. .......................................... 148/421; 420/417
[58] Field of Search ................................... 148/407, 421; 420/417

[56] References Cited

U.S. PATENT DOCUMENTS

| | | | |
|---|---|---|---|
| 3,408,604 | 10/1968 | Doi et al. | 420/417 |
| 3,597,664 | 8/1971 | Villani et al. | 317/230 |
| 3,671,226 | 6/1972 | Komata et al. | |
| 3,752,664 | 8/1973 | Steinemann | |
| 3,849,124 | 11/1974 | Villani | |
| 4,040,129 | 8/1977 | Steinemann et al. | |
| 4,253,933 | 3/1981 | Sato et al. | 204/293 |
| 4,857,269 | 8/1989 | Wang et al. | 420/417 |
| 4,952,236 | 8/1990 | Wang et al. | 75/10.14 |
| 5,169,597 | 12/1992 | Davidson et al. | 420/417 |
| 5,545,227 | 8/1996 | Davidson et al. | |

FOREIGN PATENT DOCUMENTS

| | | | |
|---|---|---|---|
| 2134926 | 1/1972 | Germany | |
| 2350199 | 7/1974 | Germany | 420/417 |
| 47-25559 | 7/1972 | Japan | 420/417 |
| 61-157652 | 7/1986 | Japan | 420/417 |
| 243841 | 5/1969 | U.S.S.R. | 420/417 |
| 1325269 | 8/1973 | United Kingdom | |

OTHER PUBLICATIONS

Beta–Titanium Alloy for Surgical Implants, S.G. Steinemann et al, Seventh World Conference on Titanium, Jun. 28 to Jul. 2, 1992.
Naspsrinoffs Already Making Positive Impact on U.S. Industries, Aviation Week & Space Technology, Jul. 27, 1992 pp. 54–55.
New Low–Modulus, High–Strength, Corruosion–Resistant Ti–13Nb–13Zr Alloy for Orthopaedic Implant Applications, Davidson et al, 77th/International Conference on BioMedical Engineering, Dec. 2–4, 1992, pp. 414–416.
Ti–13Nb–13Zr: A New Low Modulus, High Strength, Corrosion Resistant Near–Beta Alloy for Orthopaedic Implants, Ajit K. Mishra et al, Proc. Beta Titanium Symposium, TMS Annual Meeting, Denver, Colorado, Feb. 21–25, 1993.
Birth of the Betas, Aerospace America, May 1993, pp. 36–37.
Effect of Alloying Elements on Mechnanical Properties of Titanium Alloys for Medical Implants, Yoshimitsu Okasaki et al, Materials Transactions, Jim vol. 34, No. 12, 1993, pp. 1217 to 1222.

*Primary Examiner*—John Sheehan
*Attorney, Agent, or Firm*—Arthur Jacob

[57] ABSTRACT

Biocompatible titanium base alloys for medical devices which are intended to remain on or in a living human being for an extended period of time, such as surgical and medical implants. The alloys are free from toxic elements such as Al, Ni, Co, Fe, Cr, Mo, and W. They are quaternary alloys of Ti with between about 2.5% up to 13% Zr, about 20% to about 40% Nb, about 4.5% to about 25% Ta, all percentages being by weight, the balance being Ti and the total of Ta plus Nb being between about 35% and 52% by weight. The ration of Nb/Ta is between 2 and 13. These alloys may also contain limited amounts of non-toxic interstitial elements, such as C, N, and O. The relative proportions of Ti, Zr, Ta, and Nb are such that the modulus of elasticity is below 65 GPa.

15 Claims, 1 Drawing Sheet

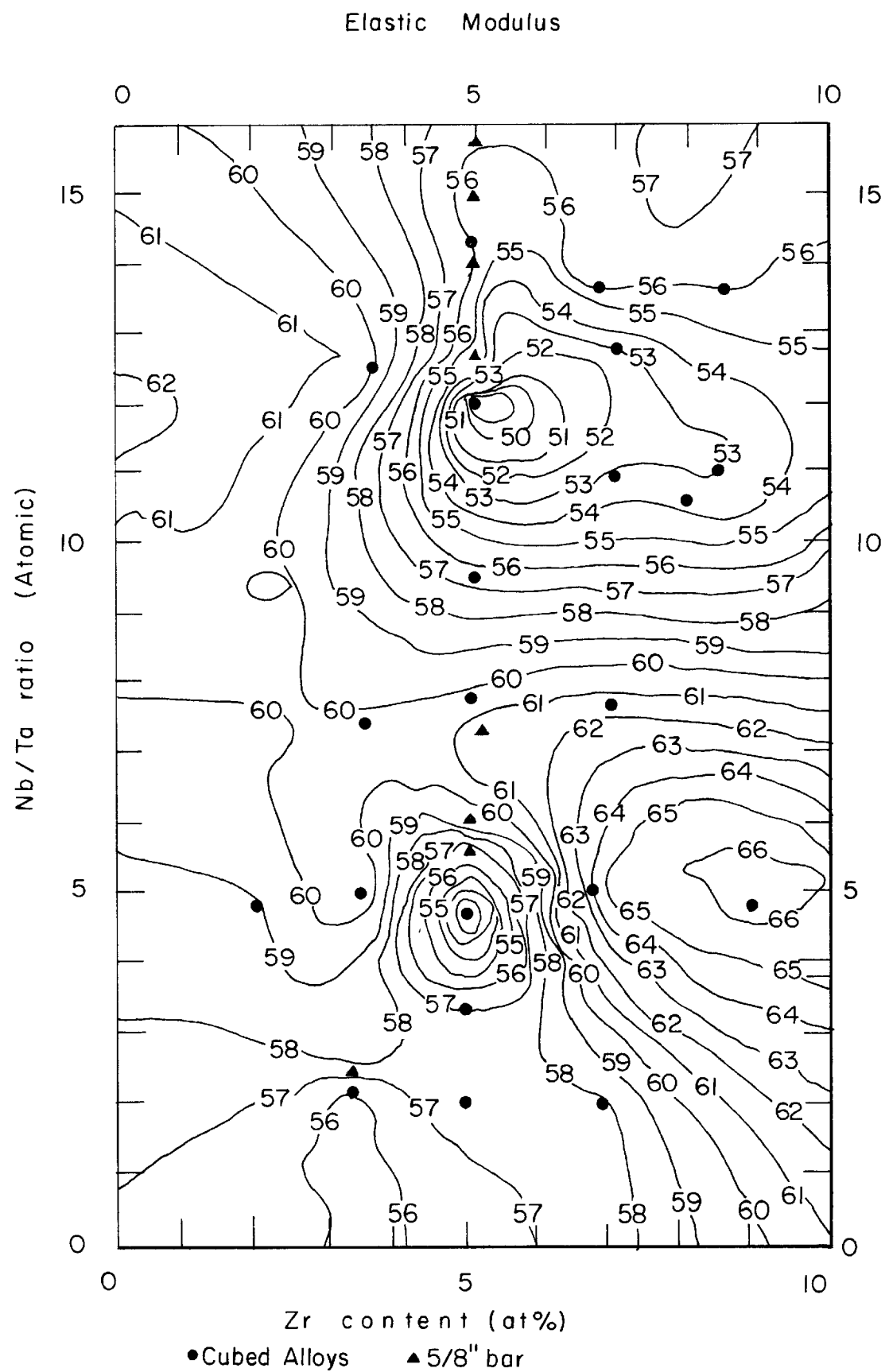

LOW MODULUS BIOCOMPATIBLE TITANIUM BASE ALLOYS FOR MEDICAL DEVICES

This application is a continuation of application Ser. No. 08/323,453 filed Oct. 14, 1994, now abandoned.

THE INVENTION

The present invention relates to biocompatible titanium base alloys which exhibit a low modulus of elasticity.

More particularly, the invention relates to biocompatible titanium base alloys with niobium, tantalum, and zirconium in such relative proportions that the resulting alloys are ductile and exhibit a stable beta (BCC) morphology, a modulus of elasticity below 70 GPa, and a tensile strength of at least 80,000 psi.

This invention relates to a family of quaternary titanium base alloys, which are composed of biocompatible elements and are free from toxic metallic elements such as Al, Fe, Ni, Co, Cr, Mo, or W, and are therefore useful in medical devices which are intended to reside on or in the human body for an extended period of time. One such device is a surgical implant, and for the purpose of illustration, the invention will be described for such a use, although it is to be understood that the alloys may have other utility, both medical and non-medical, by virtue of their chemical and physical properties.

For surgical implants it is essential that the alloys be free of elements which are toxic to human beings, and be composed entirely of elements which are biocompatible with human tissues. It is also desirable that the alloys are ductile and possess a low modulus of elasticity comparable to that of bones in the human body.

BACKGROUND OF THE INVENTION

Biocompatible titanium base alloys are described in a number of United States patents including the following:

| | |
|---|---|
| Steinemann et al | 4,040,129 issued August 09, 1973 |
| Wang et al | 4,857,269 issued August 18, 1989 |
| Wang et al | 4,952,236 issued August 28, 1990 |
| and Davidson et al | 5,169,597 issued December 02, 1992. |

The disclosures of these patents are incorporated in this application as representing the state of the art to which this invention relates and for their descriptions of such prior art.

The present invention is an improvement over the alloys described in the above noted patents insofar as it provides novel fully biocompatible alloys with a low modulus of elasticity.

In the Steinemann et al patent the toxicity of various elements are discussed and alloys of titanium and/or zirconium containing 3 to 30% by weight of at least one member selected from the group consisting of Nb, Ta, Cr, Mo, and Al are described. Several α-β alloys are described along with a number of alloys containing Al, Mo, and Cr. No quaternary alloys of Ti, Nb, Ta, and Zr are described. The presence of Al, Cr, or Mo is undesirable because of their toxicity when the alloys are utilized in medical devices, such as surgical implants. The alloys of the present invention do not contain any Al, Cr, or Mo.

The alloys described in the two Wang et al patents contain an amount up to 3% of at least one eutectoid beta stabilizer selected from the group consisting of Fe, Mn, Cr, Co, and Ni, each of which is orders of magnitude more toxic than Ti, Zr, Nb, or Ta. The alloys described in these patents possess a modulus of elasticity (E) of 66.9 to 100 GPa with most of the alloys exhibiting a modulus of elasticity between 75 and 100 GPa. Unlike the alloys of Wang et al, the alloys of the present invention do not contain any of the toxic eutectoid stabilizers required by Wang et al.

Two specific alloys are described in Davidson et al 5,169,597; namely, a Ti—13Zr—13Nb and a Ti—18Zr—6Nb alloy. These alloys exhibit a modulus less than 85 GPa, and desirably between 60 and 85 GPa. The alloys of the present invention differ from those in Davidson et al, by having lower Ti and Zr contents and a content of Ta plus Nb which results in low moduli of elasticity.

Objects

One object of the present invention is to provide new and improved alloys for medical devices intended to remain on or in a living human body for an extended period of time.

A further object is to provide new and improved biocompatible titanium base alloys which possess moduli of elasticity below about 65 GPa, and preferably between 50 and 60 GPa.

Another object is to produce biocompatible titanium base alloys of Ti, Nb, Ta, and Zr exhibiting a modulus of elasticity below 65 GPa.

A further object of the invention is to provide surgical implants composed of the novel alloys of this invention.

Still a further object of the invention, is to provide titanium base alloys consisting essentially of between about 2 and about 9 atomic percent Zr and between about 22 and 30 atomic percent of Nb plus Ta and the balance Ti, with the atomic ratio of Nb to Ta between 2 and 16. Stated in weight percent, the alloys of this invention comprise between about 2.5 up to 13% Zr, 20 to 40% Nb, 4.5 to 25% Ta, the total of Nb and Ta being between about 36.5 and 47%, the balance being Ti.

A further object is to provide biocompatible β stable titanium base alloys of Ta, Nb, and Zr which are isotropic when solution annealed.

These and other objects of the invention will be pointed out, or will become apparent from the description which follows, taken in conjunction with the drawing which is a diagram showing moduli of elasticity for Ti base alloys containing Zr, Nb, and Ta. The single FIGURE is based on the alloys set forth in Tables 1 and 2 below:

TABLE 1

Chemical compositions of alloys in atomic percent.

| Alloy # | Analyzed content | Nb + Ta | Nb/Ta | Elastic Modulus[+] GPa ± 10% | mpsi ± 10% |
|---|---|---|---|---|---|
| TA5 | Ti-17.4Nb-8.1Ta-3.4Zr | 25.5 | 2.15 | 55.3 | 8.0 |
| TA5(T-1-1)* | Ti-17.3Nb-7.2Ta-3.4Zr | 24.5 | 2.4 | 58.3 | 8.4 |
| TA6 | Ti-16.1Nb-8.2Ta-3.0Zr | 24.3 | 2.0 | 64.9 | 9.4 |
| TA7 | Ti-20.5Nb-4.5Ta-5.1Zr | 25.0 | 4.6 | 50.0 | 7.3 |
| TA7(T-3)* | Ti-20.2Nb-3.6Ta-5.0Zr | 23.8 | 5.6 | 55.7 | 8.0 |
| TA7(B-4)* | Ti-20.0Nb-3.4Ta-5.1Zr | 23.4 | 5.9 | 59.1 | 8.5 |
| TA7(T-4)* | Ti-19.5Nb-2.7Ta-5.2Zr | 22.2 | 7.2 | 59.1 | 8.5 |
| TA8 | Ti-24.1Nb-1.7Ta-5.0Zr | 25.8 | 14.2 | 55.7 | 8.1 |
| TA9 | Ti-2i.9Nb-4.5Ta-3.5Zr | 26.4 | 4.9 | 61.2 | 8.9 |
| TA10 | Ti-23.6Nb-1.9Ta-3.5Zr | 25.5 | 12.4 | 60.9 | 8.8 |
| TA11 | Ti-20.0Nb-4.0Ta-3.6Zr | 24.0 | 5.0 | 61.0 | 8.8 |
| TA12 | Ti-22.1Nb-1.7Ta-3.2Zr | 23.8 | 13.0 | 62.7 | 9.1 |
| TA13 | Ti-22.6Nb-4.5Ta-6.8Zr | 27.1 | 5.0 | 65.8 | 9.5 |
| TA14 | Ti-21.8Nb-4.5Ta-9.1Zr | 26.3 | 4.8 | 66.4 | 9.6 |
| TA15 | Ti-20.5Nb-4.0Ta-4.9Zr | 24.5 | 5.1 | 54.1 | 7.8 |
| TA16 | Ti-20.2Nb-4.0Ta-6.9Zr | 24.2 | 5.1 | 66.6 | 9.6 |
| TA17 | Ti-19.9Nb-4.1Ta.8.9Zr | 24.0 | 4.9 | 60.2 | 8.7 |
| TA18 | Ti-16.9Nb-9.1Ta-5.0Zr | 26.0 | 1.9 | 57.7 | 8.3 |
| TA19 | Ti-19.9Nb-6.1Ta-5.1Zr | 26.0 | 3.3 | 57.4 | 8.3 |
| TA20 | Ti-23.0Nb-3.0Ta-5.0Zr | 26.0 | 7.7 | 60.2 | 8.7 |
| TA21 | Ti-24.0Nb-2.6Ta-5.1Zr | 26.6 | 9.4 | 56.8 | 8.2 |
| TA22 | Ti-24.2Nb-2.0Ta-5.1Zr | 26.2 | 12.0 | 47.1 | 6.8 |
| TA22(T-2-1)* | Ti-23.8Nb-1.6Ta-5.0Zr | 25.4 | 14.9 | 54.7 | 7.9 |
| TA22(T-3-1)* | Ti-23.9Nb-1.7Ta-4.9Zr | 25.6 | 14.0 | 57.1 | 8.2 |
| TA22(T-3-2)* | Ti-24.0Nb-1.9Ta-4.9Zr | 25.9 | 12.6 | 56.1 | 8.1 |
| TA22(B-4-2)* | Ti-23.7Nb-1.5Ta-5.0Zr | 25.2 | 15.8 | 56.2 | 8.1 |
| TA23 | Ti-22.0Nb-4.6Ta-2.0Zr | 26.6 | 4.8 | 58.8 | 8.5 |
| TA24 | Ti-16.7Nb-8.7Ta-6.9Zr | 25.4 | 1.9 | 57.5 | 8.3 |
| TA25 | Ti-23.0Nb-3.1Ta-3.5Zr | 26.1 | 7.4 | 60.0 | 8.7 |
| TA26 | Ti-23.0Nb-3.0Ta-7.1Zr | 26.0 | 7.7 | 61.4 | 8.9 |
| TA27 | TI-24.5Nb-2.3Ta-7.9Zr | 26.8 | 10.6 | 53.8 | 7.8 |
| TA28 | Ti-24.2Nb-1.9Ta-6.9Zr | 26.1 | 12.7 | 51.9 | 7.5 |

TABLE 2

Chemical compositions of alloys in weight percent.

| Alloy # | Analyzed content | Nb + Ta | Nb + Ta + Zr |
|---|---|---|---|
| TA5 | Ti-23.8Nb-21.6Ta-4.6Zr | 45.4 | 50.0 |
| TA5(T-1-1)* | Ti-24.2Nb-19.5Ta-4.6Zr | 43.7 | 48.3 |
| TA6 | Ti-22.2Nb-22.2Ta-4.1Zr | 44.4 | 48.5 |
| TA7 | Ti-29.2Nb-12.4Ta-7.1Zr | 41.6 | 48.7 |
| TA7(T-3)* | Ti-29.4Nb-10.2Ta-7.1Zr | 39.6 | 46.7 |
| TA7(B-4)* | Ti-29.3Nb-9.6Ta-7.3Zr | 38.9 | 46.2 |
| TA7(T-4)* | Ti-29.0Nb-7.8Ta-7.5Ta | 36.8 | 43.3 |
| TA8 | Ti-35.5Nb-4.95Ta-6.9Zr | 40.4 | 47.3 |
| TA9 | Ti-31.1Nb-12.6Ta-4.9Zr | 43.7 | 48.6 |
| TA10 | Ti-35.1Nb-5.4Ta-5.1Zr | 40.5 | 45.6 |
| TA11 | Ti-29.0Nb-11.3Ta-5.1Zr | 40.3 | 45.4 |
| TA12 | Ti-33.3Nb-5.1Ta-4.8Zr | 38.4 | 43.2 |
| TA13 | Ti-31.4Nb-12.1Ta-9.3Zr | 43.5 | 52.8 |
| TA14 | Ti-29.9Nb-12.0Ta-12.3Zr | 41.9 | 54.2 |
| TA15 | Ti-29.5Nb-11.1Ta-6.9Zr | 40.6 | 47.5 |
| TA16 | Ti-28.8Nb-11.0Ta-9.7Zr | 39.8 | 49.5 |
| TA17 | Ti-28.0Nb-11.1Ta-12.3Zr | 39.1 | 51.4 |
| TA18 | Ti-22.5Nb-23.7Ta-6.5Zr | 46.2 | 52.7 |
| TA19 | Ti-27.5Nb-16.4Ta-6.9Zr | 43.9 | 50.8 |
| TA20 | Ti-33.2Nb-8.4Ta-6.9Zr | 41.6 | 48.5 |
| TA21 | Ti-34.7Nb-7.2Ta-7.3Zr | 41.9 | 49.2 |
| TA22 | Ti-35.3Nb-5.7Ta-7.3Zr | 41.0 | 48.3 |
| TA22(T-1-1)* | Ti-35.3Nb-4.5Ta-7.3Zr | 39.8 | 47.1 |
| TA22(T-3-1)* | Ti-35.2Nb-4.9Ta-7.2Zr | 40.1 | 47.3 |
| TA22(T-3-2)* | Ti-35.3Nb-5.1Ta-7.1Zr | 40.4 | 47.5 |
| TA22(B-4-2)* | Ti-35.1Nb-4.4Ta-7.3Zr | 39.5 | 46.3 |
| TA23 | Ti-31.5Nb-12.8Ta-2.9Zr | 44.3 | 47.2 |
| TA24 | Ti-22.2Nb-22.5Ta-9.0Zr | 44.7 | 53.7 |
| TA25 | Ti-33 4Nb-8.8Ta-5.0Zr | 42.2 | 47.2 |
| TA26 | Ti-32 7Nb-8.4Ta-9.9Zr | 41.1 | 51.0 |
| TA27 | Ti-34.8Nb-6.5Ta-11.0Zr | 41.3 | 52.3 |
| TA28 | Ti-35.0Nb-5.3Ta-9.8Zr | 40.3 | 50.1 |
| TA30L | Ti-34.5Nb-6.2Ta-9.7Zr | 40.7 | 50.4 |
| TA30H | Ti-33.9Nb-6.0Ta-9.6Zr-0.22O | 39.9 | 49.5 |
| TA30ExH | Ti-34.5Nb-6.2Ta-9.8Zr-0.43O+ | 40.7 | 50.5 |
| TA31 | Ti-34.2Nb-6.1Ta-11.7Zr | 40.3 | 52.0 |
| TA32L | Ti-35.3Nb-5.0Ta-9.9Zr | 40.3 | 50.2 |
| TA32H | Ti-35.1Nb-5.0Ta-9.9Zr-0.23O | 40.1 | 50.0 |
| TA33 | Ti-35.0Nb-4.9Ta-11.8Zr | 39.9 | 51.7 |

*samples from ⅝" rolled bar. + Total interstitial content (O + N + C) 0.437 wt %
All alloys except those having names ending with letter H and ExH have a total interstitial content of 0.05 wt %.

Tables 1 and 2 describe alloys of the present invention prepared from pure elemental metals which were melted in either an arc or plasma furnace to form the desired composition. The resulting ingot may be forged or machined to the shape of the device in which the alloy is to be used. Solution heat treatment to ensure an all β structure, or a combination of heat treatment and/or working may be employed to produce an α-β alloy if such is desired.

Without adversely affecting their low modulus of elasticity, the biocompatible titanium-zirconium-niobium-tantalum alloys of this invention may also include one or more non-toxic interstitial elements (C,N, and O) for the beneficial effects these elements have on the physical properties of the alloys. The total amounts of these elements which may be added to the alloys of this invention should not exceed 0.5% by weight.

The drawing is a plot of moduli of elasticity for the titanium based alloys of Tables 1 and 2 with 2 to 9 atomic percent Zr, 22 to 27 atomic percent Ta plus Nb, and various atomic ratios of Nb/Ta between 1.9 and 16.

Referring now to the drawing, it will be seen that the quaternary alloys of the present invention contain between 2 and 9 atomic percent Zr, Nb/Ta ratios from 1.9 to 16, and exhibit moduli of elasticity between 47.1 and 66.4 GPa. Particularly preferred alloys are those with the lowest moduli of elasticity, as shown on the graph. Three such preferred alloys described in the tables are TA5, TA7, and TA22 with the following compositions, in weight percent:

| | | | |
|---|---|---|---|
| 23.8 Nb | 21.6 Ta | 4.6 Zr | balance Ti |
| 29.2 Nb | 12.4 Ta | 7.1 Zr | balance Ti |
| 35.3 Nb | 5.7 Ta | 7.3 Zr | balance Ti |

It should be noted that superconducting alloys of Ti containing one or more of the elements Ta, Nb, and Zr are described in Collings "Sourcebook of Titanium Alloy Superconductivity" published by Plenum Press, New York and London (1983), and in German Offenlegungschrift 2 350 199. Nowhere in these disclosures is there any suggestion that the superconductive alloys would be useful in medical devices in which a low modulus of elasticity would be a desirable property.

Implants fabricated from the alloys of this invention may be coated or given other surface treatments such as passivation to enhance their utility.

Having now described preferred embodiments of the invention it is not intended that it be limited except as required by the appended claims.

We claim:

1. A medical device for use in the human body, the medical device having been fabricated from an isotropic, biocompatible titanium base alloy consisting essentially of between 2.5% and 13% by weight Zr, between 20% and 40% by weight Nb, between 4.5% and 25% by weight Ta, and the balance Ti, with the weight of Nb plus Ta being between 35% and 52%, and the atomic ratio of Nb/Ta being between 1.9 and 16, the relative proportions of Ti, Zr, Ta, and Nb being such that the modulus of elasticity is below about 65 GPa.

2. The invention of claim 1 in which the alloy consists essentially of 29.2% Nb, 12.4% Ta, 7.1% Zr, by weight, and the balance Ti.

3. The invention of claim 1 in which the alloy consists essentially of 23.8% Nb, 21.6% Ta, 4.6% Zr, by weight, and the balance Ti.

4. The invention of claim 1 in which the alloy consists essentially of 35.3% Nb, 5.7% Ta, 7.3% Zr, by weight, and the balance Ti.

5. The invention of claim 1 in which the Nb plus Ta content is between 38% and 46% by weight.

6. The invention of claim 1 in which the Ti content is between 46% and 58% by weight.

7. The invention of claim 1 in which the alloy contains up to 0.5% by weight total of at least one interstitial element selected from the group consisting of C, N, and O, in addition to the Ti, Zr, Nb, and Ta.

8. The invention of claim 1 wherein the medical device is a surgical implant.

9. The invention of claim 1 wherein the medical device is a prosthetic implant.

10. The invention of claim 1 in which the alloy consists essentially of between about 2 atomic percent and 9 atomic percent Zr, between about 22 atomic percent and 30 atomic percent Nb plus Ta, and the balance Ti, with the atomic ratio of Nb/Ta being between 1.9 and 16.

11. The invention of claim 1 in which the alloy has been solution annealed.

12. The invention of claim 11 in which the Zr content is between about 4 atomic percent and about 7 atomic percent, the Ta plus Nb content is between about 22 atomic percent and 28 atomic percent, and the modulus of elasticity is below about 58 GPa.

13. The invention of claim 11 in which the Nb/Ta atomic ratio is between about 4 and 6.

14. The invention of claim 11 in which the Nb/Ta atomic ratio is between about 10 and 14.

15. The invention of claim 1 in which the modulus of elasticity is below 57 GPa, as shown in the accompanying FIGURE.

* * * * *